United States Patent
Tate et al.

(10) Patent No.: US 12,356,991 B2
(45) Date of Patent: Jul. 15, 2025

(54) AQUEOUS SOLUTIONS OF POORLY SOLUBLE ACTIVE INGREDIENTS USING POLYALKYOXYLATED AMINO ALCOHOLS

(71) Applicant: Dow Global Technologies LLC, Midland, MI (US)

(72) Inventors: Michael P. Tate, Midland, MI (US); Thomas H. Kalantar, Midland, MI (US); Michael L. Tulchinsky, Midland, MI (US); David Brennan, Midland, MI (US); Adam H. Xiong, Mount Pleasant, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 1020 days.

(21) Appl. No.: 17/294,860

(22) PCT Filed: Nov. 25, 2019

(86) PCT No.: PCT/US2019/062949
§ 371 (c)(1),
(2) Date: May 18, 2021

(87) PCT Pub. No.: WO2020/123129
PCT Pub. Date: Jun. 18, 2020

(65) Prior Publication Data
US 2022/0007645 A1    Jan. 13, 2022

Related U.S. Application Data

(60) Provisional application No. 62/777,816, filed on Dec. 11, 2018.

(51) Int. Cl.
| | | |
|---|---|---|
| A01N 43/653 | (2006.01) |
| A01N 25/02 | (2006.01) |
| A01N 25/30 | (2006.01) |
| A01N 47/20 | (2006.01) |
| A01P 3/00 | (2006.01) |
| A61K 47/10 | (2017.01) |
| A61K 47/18 | (2017.01) |

(52) U.S. Cl.
CPC ........... *A01N 43/653* (2013.01); *A01N 25/02* (2013.01); *A01N 25/30* (2013.01); *A01N 47/20* (2013.01); *A01P 3/00* (2021.08); *A61K 47/10* (2013.01); *A61K 47/18* (2013.01)

(58) Field of Classification Search
CPC ...... A01N 43/653; A01N 25/02; A01N 25/30; A01N 47/20; A01P 3/00; A61K 47/10; A61K 47/18
See application file for complete search history.

(56) References Cited

U.S. PATENT DOCUMENTS

| | | |
|---|---|---|
| 6,451,731 B1 | 9/2002 | Agbaje et al. |
| 7,407,667 B2 | 8/2008 | Zerrer et al. |
| 7,655,599 B2 | 2/2010 | Rochling et al. |
| 7,776,360 B2 | 8/2010 | Kipp et al. |
| 7,977,278 B2 | 7/2011 | Vermeer et al. |
| 9,204,643 B2 | 12/2015 | Hopkins |
| 9,592,294 B2 | 3/2017 | Ladika et al. |
| 9,681,658 B2 * | 6/2017 | Blease .................. C08G 63/78 |
| 2008/0312290 A1 | 12/2008 | Vermeer et al. |
| 2012/0021914 A1 | 1/2012 | Berghaus et al. |
| 2013/0237641 A1 | 9/2013 | Riff et al. |
| 2015/0374823 A1 | 12/2015 | Ladika et al. |
| 2016/0235071 A1 | 8/2016 | Jadhav et al. |
| 2016/0289590 A1 | 10/2016 | Pierre et al. |

FOREIGN PATENT DOCUMENTS

| | | | | |
|---|---|---|---|---|
| CN | 108929424 A | * | 12/2018 | ......... C08G 18/3275 |
| WO | WO-0194001 A2 | * | 12/2001 | ............ A01N 25/28 |
| WO | 2012018885 A1 | | 2/2012 | |
| WO | WO-2014080190 A1 | * | 5/2014 | ............ A01N 25/00 |

OTHER PUBLICATIONS

Cole, E. T., Advanced Drug Delivery Reviews 60 (2008), pp. 747-756.
International Preliminary Report on Patentability for the correspodning International Application No. PCT/US2019/062949, Mailing date: Oct. 13, 2020; 16 pages.
International Search Report for the corresponding International Application No. PCT/US2019/062949; International Filing Date: Nov. 25, 2019, Date of Mailing: Feb. 12, 2020; 7 pages.
Kalantar et al., "Novel Excipient Solubilizers for Poorly Soluble Drugs", Controlled Release Society, Jul. 13-16, 2017; 1 page.
Written Opinion for the corresponding International Application No. PCT/US2019/062949, International Filing Date: Nov. 25, 2019, Date of Mailing: Feb. 12, 2020; 9 pages.

* cited by examiner

*Primary Examiner* — James H Alstrum-Acevedo
*Assistant Examiner* — Manahil Mirghani Ali Abdalhameed
(74) *Attorney, Agent, or Firm* — CANTOR COLBURN LLP

(57) ABSTRACT

Disclosed is the use a polyalkoxylated amino alcohol to solubilize active compounds that are poorly soluble in water, including particularly agricultural actives or pharmaceutical actives. Also disclosed are compositions comprising such actives, water and the polyalkoxylated aminoalcohol.

18 Claims, No Drawings

AQUEOUS SOLUTIONS OF POORLY SOLUBLE ACTIVE INGREDIENTS USING POLYALKYOXYLATED AMINO ALCOHOLS

CROSS-REFERENCE TO RELATED APPLICATIONS

This application is a National Stage application of PCT/US2019/062949, filed Nov. 25, 2019, which claims benefit of U.S. Application No. 62/777,816 filed on Dec. 11, 2018, both of which are incorporated by reference herein in their entirety.

FIELD OF THE INVENTION

The field of this invention is aqueous solutions of poorly soluble active ingredients using polyalkyoxylated amino alcohols.

BACKGROUND

It is often desirable to utilize certain types of active materials in aqueous solution. For example, it can be desirable to have and dispense certain pharmaceuticals in aqueous solution. As another example, it can be desirable to dispense agricultural chemicals such as pesticides and herbicides in a spray on aqueous solution. However, some of these materials are not soluble at the concentrations which provide effective dosages.

Various approaches have been proposed to obtain various aqueous stable agricultural chemical formulations (see e.g. U.S. Pat. Nos. 6,451,731; 9,204,643; US20160235071; U.S. Pat. Nos. 7,977,278; 7,407,667; 7,655,599; US 20080312290, and WO2012/18885). Various approaches have also been proposed for solubilizing pharmaceutical actives (See e.g. U.S. Pat. Nos. 9,592,294; 7,776,360; Novel Excipient Solubilizers for Poorly Soluble Drugs, Kalantar et. al. Controlled Release Society, Jul. 13-16, 2017).

Nevertheless, a need remains for effective means of controlling precipitation of poorly water soluble biologically active compounds.

SUMMARY OF THE INVENTION

Disclosed herein is the use of polyalkoxylyated amino alcohols to enhance solubility of active ingredients that are poorly soluble in water or aqueous media. Specifically, disclosed is a composition comprising a biologically active compound that is insoluble or poorly soluble in water and a polyalkoxylated amino alcohol of the formula

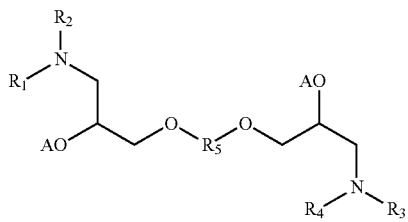

where $R_1$, $R_2$, $R_3$, and $R_4$ are independently selected from alkyl, alkenyl, aryl, aralkyl, or heterocyclic groups having 1-25 carbons, $R_5$ is a divalent alkyl, alkenyl, aryl, aralkyl, or heterocyclic group having 4-25 carbons, and where each AO is a polyoxyalkylene chain having oxypropylene (PO) groups and oxyethylene (EO) groups, where m is the average number of PO groups per AO group and n is the average number of EO groups per AO group, and m is at least 1, n is at least 2, and m+n no more than 400.

DETAILED DESCRIPTION OF THE INVENTION

Disclosed herein is the use of polyalkoxylyated amino alcohols to enhance processability or efficacy of water insoluble or poorly soluble biologically active compounds. Biologically active compounds are compounds which have a negative or positive impact on a living organism by interacting chemically with a living organism. Biologically active compounds include pharmaceutical actives (also referred to as active pharmaceutical ingredients or APIs) which are any substance for application in a therapeutic, diagnostic or prophylactic medical treatment of the human or animal body and (e.g. drugs) or agricultural active ingredients which are a chemical used in agriculture, horticulture and pest management for protection of crops, plants, structures, animals and humans against unwanted organisms such as fungal and bacterial plant pathogens, weeds, insects, mites, algae, nematodes and the like. Specifically, active ingredients used for these purposes include fungicides, bactericides, herbicides, insecticides, miticides, algaecides, nematocides and fumigants. The term "agricultural active ingredient" also includes insect repellants and attractants and pheromones, modifiers of plant physiology or structure, zoospore attractants and herbicide safeners.

As used herein biologically active compounds are considered poorly soluble if they precipitate or crystallize at concentrations at which the use is desired. For example, if a compound is most useful at concentrations or dosages of 50 mg/L but significant precipitation occurs at 20 mg/L that compound would be considered poorly soluble. Thus, the biologically active compound can have a solubility in water or aqueous medium of up to 1000, up to 700, up to 500, up to 300, up to 200, up to 100, up to 50, up to 40, up to 30, up to 20 or up to 10 parts per million. In the alternative, the biologically active compound can have a solubility in aqueous medium or water of up to 50, or up to 20 or up to 10 or up to 1 mg/L.

The solubility of the biological active in an aqueous medium can be determined quantitatively e.g. by turbidity as shown in the examples below or by high pressure liquid chromatography. In the latter method for example, a solid biological active (potentially with solid excipients) is placed in an aqueous medium, after stirring for a period of time the a sample would be injected into an HPLC system with an appropriate column and the area at the expected retention time based on a control sample of the active at a known concentration is evaluated.

The polyalkoxylated amino alcohol has the formula

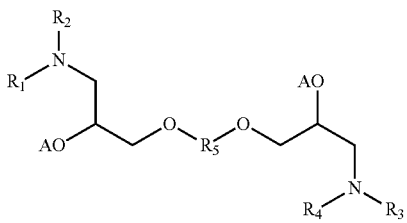

where $R_1$, $R_2$, $R_3$, and $R_4$ can be independently selected from alkyls of from 1 or from 2 or from 3 or from 4 to 25 or to 15 to 13 or to 12 or to 10 carbon atoms, alkenyls of from 2 or from 3 or from 4 to 25 or to 15 or to 13 or to 12 to 10 carbon atoms, aryls of 6 to 24 or to 12 carbon atoms, aralkyls of 7 to 25 or to 12 carbon atoms, or heterocyclic groups having 1-25 carbons, $R_5$ can be a divalent alkyl from 4 to 25 or to 15 to 13 or to 12 or to 10 carbon atoms, alkenyl from 4 to 25 or to 15 to 13 or to 12 or to 10 carbon atoms, aryl of 6 to 24 or to 12 carbon atoms, aralkyl 7 to 25 or to 12 carbon atoms, or heterocyclic group having 4-25 carbons, and where each AO is a polyoxyalkylene chain having oxypropylene (PO) groups (e.g. —($C_3H_6$)—O—) and oxyethylene (EO) groups (e.g. —$C_2H_4$O—). The number of PO groups in each AO group may be the same or different. The number of EO groups in each AO group may be the same or different. "m" is the average number of PO groups per AO group. "n" is the average number of EO groups per AO group. "m" is at least 1, "n" is at least 2, and m+n is no more than 400. $R_1$, $R_2$, $R_3$, and $R_4$ can be independently in each occurrence alkyl groups. For example, $R_1$, $R_2$, $R_3$, and $R_4$ can be butyl or ethylhexyl groups. $R_1$, $R_2$, $R_3$, and $R_4$ can be independently in each occurrence aryl groups, aralkyl groups. $R_5$ can be a divalent group comprising 1 or 2 aromatic rings such as a diphenyl, diphenylmethane, diphenylethane, or the like and having from 6 to 25 or to 20 or to 18 carbon atoms (i.e., 6-25 or 6-20 or 6-18 carbon atoms). For example, $R_5$ with the adjacent oxygens can be derivative of bisphenol A. Alternatively, $R_5$ can be an aliphatic group having linear groups or cyclic groups or a combination of linear and cyclic groups and having from 3 or from 4 to 20 or to 18 or to 15 carbon atoms. For example, $R_5$ can be 2,2-isopropylidenediphenylene, 2,2-isopropylidenedicyclohexylidene or 1,4-butylene.

The AO can be blocky in that it can have an EO rich block and a PO rich block. By EO rich block is meant that more than 50, more than 55, more than 60, more than 65, more than 70, more than 75, more than 80, more than 85, more than 90 or more than 95% of the groups in the block are EO groups. EO rich blocks are helpful in ensuring good water solubility. By PO rich block is meant that more than 50, more than 55, more than 60, more than 65, more than 70, more than 75, more than 80, more than 85, more than 90 or more than 95 of the groups in the block are PO groups. Alternatively, the AO group can be a block copolymer having separate EO blocks and PO blocks.

In determining "m" and "n" (e.g. by NMR) one can determine the total number of PO groups/molecule and EO groups/molecule. Then one can divide by the number of AO groups per molecule to get the averages which are "m" and "n". The minimum value of m can be 1, 2, 3, 4, 5, 7, 10, 12, 15, 18 or 20. The maximum value of m can be 100, 90, 80, 70, 60, or 50. For example, m could be from 1 to 100, 1 to 90, or 5 to 90. The minimum value of n can be 2, 3, 4, 5, 10, 15, 20, 25, 30, or 40. The maximum value of n can be 150, 130, 110, 100, 90, 80, or 70. m/n is preferably <1. m+n according can have a minimum value of 3, 5, 10, 20, 30, 40 or 50 and a maximum value of 400, 350, 300, 250, 200, or 150.

The biological active (e.g. agricultural active) and polyalkoxylated amino alcohol can be present in weight ratios in the range from 10:1 or from 5:1 or from 1:1 or from 1:2 to 1:100, or to 1:50, or to 1:20, or to 1:10, or to 1:5. The mole ratio of biological active to polyalkoxylated amino alcohol can be from 1:1 or from 1:2 to 1:20 or to 1:10.

The composition can be a liquid comprising the biological active and the polyalkoxylated amino alcohol in an aqueous medium. In that situation, the concentration of the combination of the biological active and the polyalkoxylated amino alcohol is at least 10 or at least 50 or at least 100 or at least 200 parts per million (ppm) by weight and is no more than 10 or no more than 5 or no more than 1 parts per hundred (pph) by weight.

In the agricultural space, the use of the polyalkoxylated amino alcohol can assist in the use of poorly water soluble agricultural active ingredients, for example, in spray applications on agricultural fields, orchards or the like. For example, the use of the polyalkoxylated amino alcohol can inhibit flash precipitation that would occur if a solvent based formulation is diluted with water or can enhance solubility of solid actives. The use of the polyalkoxylated amino alcohol may provide one or more of the following benefits, for example, 1) extended stability of aqueous agricultural active systems compared to systems that do not contain the polyalkoxylated amino alcohols; 2) produce a controlled precipitation of the agricultural active ingredient generating a controlled fine particle size distribution; 3) produce finer agricultural active ingredient particles, droplets, or precipitates in aqueous systems that do not plug nozzles and present slower settling rates compared to systems that do not contain the polyalkoxylated amino alcohols; and/or 4) hinder and/or delay the formation of large precipitates that generate problems for spray applications. In addition, the enhanced solubility could enhance efficacy if for example the mode of action includes uptake of the agricultural active ingredient by the plant or animal which uptake is enhanced by higher concentration of the active in solution or if more uniform distribution is required than is attainable by particulates.

Examples of insecticides include antibiotic insecticides such as allosamidin and thuringensin, macrocyclic lactone insecticides such as spinosad, spinetoram and 21-butenyl spinosyns; avermectin insecticides such as abamectin, doramectin, emamectin, eprinomectin, ivermectin and selamectin; milbemycin insecticides such as lepimectin, milbemectin, milbemycin oxime and moxidectin; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluoro silicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as a-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate; insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as imicyafos and mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, ioethanomethrin, cyclethrin, cycloprothrin, cyfluthrin, betacyfluthrin, cyhalothrin, gamma-cyhalothrin, lambda-cyhalothrin, cypermethrin, alphacypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; ryanodine receptor insecticides such as flubendiamide, chlorantraniliprole (rynaxypyr) and cyantranilipole; tetronic acid insecticides such as spirodiclofen, spiromesifen and spirotetramat; thiourea insecticides such as diafenthiuron; urea insecticides such as flucofuron and sulcofuron; sulfoximine insecticides such as sulfoxaflor and unclassified insecticides such as closantel, crotamiton, EXD, fenazaflor, fenazaquin, fenoxacrim, fenpyroximate, flubendiamide, hydramethylnon, isoprothiolane, malonoben, metaflumizone, metoxadiazone, nifluridide, pyridaben, pyridalyl, pyrifluquinazon, rafoxanide, triarathene and triazamate. Insecticides can be chosen based on water solubilities published in compendia such as The Pesticide Manual Fourteenth Edition, (ISBN 1-901396-14-2), which is incorporated herein by reference in its entirety. Future editions of The Pesticide Manual will also be useful for selecting insecticides which may benefit from being used with the polyalkoxylated amino alcohols as disclosed herein.

Examples of fungicides include ametoctradin, amisulbrom 2-(thiocyanatomethylthio)-benzothiazole, 2-phenylphenol, 8-hydroxyquinoline sulfate, antimycin, azaconazole, azoxystrobin, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, BYF 1047, calcium polysulfide, captafol, captan, carbendazim, carboxin, carpropamid, carvone, chloroneb, chlorothalonil, chlozolinate, copper hydroxide, copper octanoate, copper oxychloride, copper sulfate, copper sulfate (tribasic), cuprous oxide, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, meptyl dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, fluxapyrad, folpet, formaldehyde, fosetyl, fosetyl-aluminium, uberidazole, furalaxyl, furametpyr, guazatine, guazatine acetates, GY-81, hexachlorobenzene, hexaconazole, hymexazol, imazalil, imazalil sulfate, imibenconazole, minoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, meptyldinocap, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothalisopropyl, nuarimol, octhilinone, ofurace, oleic acid (fatty acids), orysastrobin, oxadixyl, oxine-copper, oxpoconazole fumarate, oxycarboxin, penflufen, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyraxostrobin, pyrazophos, pyribencarb, pyributicarb, pyrifenox, pyrimethanil, pyriofenone, pyrometostrobin, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-048, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazolopyrimidine, triazoxide, tricyclazole, tridemorph, trifloxystrobin, triflumizole, triforine, triticonazole, validamycin, valiphenal, valifenate, vinclozolin, zineb, ziram, zoxamide, (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, urcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, hosdiphen, prothiocarb; prothiocarb hydrochloride, pyracarbolid, pyridinitril, pyroxychlor, pyroxyfur, quinacetol; quinacetol sulfate, quinazamid, quinconazole, abenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, UK-2A, derivatives of UK-2A such as, for example, (3S,6S,7R,8R)-8-benzyl-3-(3-(isobutyryloxymethoxy)-4-methoxypicolinamido)-6-methyl-4,9-dioxo-1,5-dioxonan-7-yl isobutyrate which has a CAS Registry Number of 328255-92-1 and will be referred to herein as 328255-92-1, urbacid, XRD-563, zarilamid, IK-1140, and propargyl amides. Fungicides can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting fungicides for combination with the alkyoxylated amino alcohols as disclosed herein.

Examples of herbicides include amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such asimazamethabenz, imazamox, imazapic, imazapyr, imazaquin and imazethapyr; nitrile herbicides such as bromobonil, bromoxynil, chloroxynil, dichlobenil, iodobonil, ioxynil and pyraclonil; organophosphorus herbicides such as amiprofosmethyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, fluroxypyr-meptyl, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. Herbicides can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting herbicides for combination with the alkyoxylated amino alcohols.

Examples of modifiers of plant physiology or structure include ancymidol, aminoethoxyvinylglycine, 6-benzylaminopurine, carvone, chlorflurenol-methyl, chlormequat chloride, cloxyfonac, 4-CPA, cyclanilide, cytokinins, daminozide, dikegulac, ethephon, flurenol, flurprimidol, forchlorfenuron, gibberellic acids, gibberellins, inabenfide, indol-3-ylacetic acid, 4-indol-3ylbutyric acid, maleic hydrazide, mepiquat chloride, 1-methylcyclopropene, 2-(1-napthyl)acetamide, 1-napthylacetic acid, 2-napthyloxyacetic acid, nitrophenolates, paclobutrazol, Nphenylphthalamic acid, prohexadione-calcium, n-propyl dihydrojasmonate, thidiazuron, tribufos, trinexepac-ethyl, and uniconazole. Modifiers can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting modifiers of plant physiology or structure for combination with alkoxylated amino alcohols.

Examples of herbicide safeners, include safeners such as benoxacor, benthiocarb, brassinolide, cloquintocet (mexyl), cyometrinil, cyprosulfamide, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenylsulfonylbenzoic acid amides.

In agricultural applications, for example, the formulation may also comprise a water miscible solvent or a solvent that is soluble in water in amounts of from 0.5 or from 1 or from 2 or from 3 or from 4 or from 5 or from 10 weight percent up to 30 or up to 20 weight percent based on total weight of water and solvent. Such solvents include glycol ethers, alcohols and ketones and they are miscible or soluble depending upon the size of the hydrocarbyl groups. Water miscible solvents include N-Methyl-2-pyrrolidone, ethylene glycol monobutyl ether, ethyl lactate, gamma-butyrolactone, propylene glycol, propylene glycol methyl ether, tetrahydrofurfuryl alcohol, 2-ethoxyethanol, dimethyl sulfoxide, 1-methoxy-2-propanol, 2-butoxyethanol, dipropylene glycol methyl ether, n-propanol, and acetone. Water soluble solvents include acetophenone, butyl lactate, cyclohexanone, propylene carbonate, methyl isobutyl ketone, n-butanol, ethylene glycol n-butyl acetate, ethylene glycol phenyl ether. Applications that are "in-can" applications frequently include such a solvent. This formulation may further include water or may be diluted with water prior to application to the intended area where herbicidal or pesticidal protection is desired. Without the presence of the polyalkoxylated amino alcohol, the dilution with water might cause the poorly soluble active to precipitate. Where solvent is present the weight ratio of solvent to water can be at least 0.1:99.9 or at least 1:99 or at least 5:95 or at least 10:90 and is no more than 99:1 or no more than 90:10 or no more than 80:20 or no more than 70:30 or no more than 60:40 or no more than 50:50.

The formulation could alternatively be in solid particles which are added to a tank with water prior to application to the location where the herbicide or pesticide protection is desired (e.g. field or warehouse). This embodiment could be formed by mixing the polyalkoxylated amino alcohol and pesticide together such as by dissolving in a common solvent and removing that solvent, or by spray drying together, or other such means to make a solid or semi-solid composition that can be diluted in a tank for application to a crop or field.

The aqueous solution including the active and the polyalkoxylated amino alcohol can be applied by spraying.

Other potential ingredients in an agricultural active containing formulation may be inactive or inert ingredients such as dispersants, thickening agents, stickers, film-forming agents, buffers, emulsifiers, anti-freezing agents, dyes, stabilizers, solid carriers and the like may also be incorporated into formulations. Those additional ingredients, can be present, individually and/or cumulatively in amounts of less than 10 or less than 8 or less than 5 or less than 3 or less than 2 or less than 1 weight percent and 0 weight percent or at least 0.1 or at least 0.5 based on total weight of the composition.

In the pharmaceutical space, the use of the polyalkoxylated amino alcohols can enable solubilization of poorly water soluble active pharmaceutical ingredients to enhance processability in manufacture of tablets and the like (e.g. by spray drying). In addition, poor aqueous solubility of pharmaceutical actives (also referred to as active pharmaceutical ingredients or APIs) can lead to lower bioavailability and efficacy.

The active pharmaceutical ingredient can generally be any substance for application in a therapeutic, diagnostic or prophylactic medical treatment of the human or animal body. The API may for instance be selected from the group of antihypertensives, anti-anxiety agents, anticlotting agents, anticonvulsants, blood glucose lowering agents, decongestants, antihistamines, antitussives, beta blockers, anti-inflammatories, antipsychotic agents, cognitive enhancers, cholesterol-reducing agents, antiobesity agents, autoimmune disorder agents, anti-impotence agents, antibacterial agents, antifungal agents, hypnotic agents, anti-Parkinsonism agents, anti-Alzheimer's disease agents, anti-depressants, antiviral agents, anti-atherosclerotic agents, glycogen phosphorylase inhibitors, hormones, vitamins, carotinoids, antiseptic agents, cytostatics, anesthetics, neuroleptics, antimycotics, spasmolytic agents, immunoglobines, sera, thyroid therapeutic agents, antihyperkinetic agents, ophthalmic agents, neuropathy agents, metabolic regulators, muscle relaxants, anti-lipemics, hepatic therapeutic agents, coronary agents, cardiacs, regulatory peptides and enzymes and their inhibitors, sedatives, gynecological agents, gout remedies, fibrinolytics, circulation-promoting agents, diuretics, diagnostic agents, corticoids, bile duct therapeutics, antiasthmatics, anti-epileptics, antidotes, antidiabetes agents, antiallergics, analgesics, analeptics, keratolytic agents, antipyretic agents and vasodilatory agents, without being limited thereto. As disclosed herein, the use of the polyalkoxylated amino alcohols may be particularly useful for APIs which are poorly soluble in aqueous medium such as a class II drug according to the Biopharmaceutics Classification System (BCS) as these substances typically suffer from an insufficient bioavailability.

In addition to the polyalkoxylated amino alcohol and the API, the pharmaceutical composition can comprise further one or more physiologically compatible additives. Any conventional additives used in pharmaceutical compositions known from the prior art can be employed as long as they do not interfere with the action of the active pharmaceutical ingredient and do not adversely affect the above-described favorable effects imparted by the polyalkoxylated alcohol. If present in the inventive pharmaceutical composition, the at least one optional additive may for instance be selected from the group of fillers, pH regulators, solvents, surfactants, antioxidants, preservative agents, plasticizers, coloring agents, flavoring agents, mineral adjuvants, emollients, lubricants, perfumes and excipients other than the polyalkoxylated alcohols according to the present invention and mixtures of any of the foregoing. Suitable antioxidants can be exemplified by ascorbic acid, citric acid, vitamin E and derivatives of these compounds, as well as butylated hydroxyanisole. As plasticizer for instance mineral oils, petrolatum, lanolin, polyethylene glycol, polypropylene glycol, sorbitol, triethanol amine, benzyl benzoate, dibutyl sebacate, diethyl phthalate, glyceryl monostearate, triacetin and/or triethyl citrate could be used. Suitable solvents are e.g. water, alcohols such as ethanol, isopropyl alcohol, ethylene glycol, propylene glycol, polyethylene glycol, polypropylene glycol and glycerol. Eligible pH regulators can be all types of physiologically acceptable acids and/or bases. Suitable surfactants can be nonionic, cationic, anionic or of the betain type. For example fatty alcohol sulfates, fatty alcohol sulfonates, fatty alcohol ether sulfates, fatty alcohol ether sulfonates, fatty alcohol alkoxylates, fatty alcohol phosphates, fatty acid sulfonates, alkyl sulfonates, alkyl polyglycosides, sorbitan esters and alkoxylated derivatives thereof, sugar fatty acid esters, fatty acid polyglycerol esters, fatty acid partial glycerides, fatty acid carboxylates, fatty alcohol succinates, quarternary ammonium compounds, alkylphenol alkoxylates or mixtures thereof could be used, without being limited thereto. Fillers that may be incorporated in the pharmaceutical composition of the present invention e.g. to modify the consistency or appearance include, without being limited thereto, for instance pigments, titania, alumina, silica, zinc oxide, magnesium stearate, silicates, alumosilicates, clay, talc, waxes and polymers e.g. cellulose derivatives such as methyl cellulose, ethyl cellulose, hydroxyethyl cellulose or hydroxypropyl methylcellulose. Excipients other than the polyalkoxylated alcohols according to the present invention can be exemplified for instance by the substances mentioned as excipients in the Handbook of Pharmaceutical Excipients, Third Edition, Edited by A. H. Kibbe, American Pharmaceutical Association and Pharmaceutical Press (2000), WO 00/76482 and Tables 3-5 in E. T. Cole et al., Advanced Drug Delivery Reviews 60 (2008), 747-756.

The composition can comprise the at least one active pharmaceutical ingredient and the at least one polyalkoxylated amino alcohol together in a combined amount corresponding to 1 to 100 wt. %, preferably at least 10 wt. %, more preferably at least 50 wt. % based on the total weight of the composition. The remainder of the pharmaceutical composition may then comprise physiologically compatible additives, if any. Such additives may thus e.g. comprise 0 to 99 wt. %, preferably 0 to 90 wt. % or 0 to 50 wt. % based on the total weight of the pharmaceutical composition. The relative amount of the at least one active pharmaceutical ingredient and the at least one polyalkoxylated alcohol can be in a weight ratio in the range from 10:1 to 1:100 of active pharmaceutical ingredient(s):the polyalkoxylated alcohol, preferably from 5:1 to 1:10, more preferably from 1:1 to 1:3. The at least one polyalkoxylated alcohol can be present in the pharmaceutical composition in an amount of more than 5 wt. %, preferably at least 10 wt. %, more preferably at least 25 wt. most preferably at least 50 wt. %, based on the total weight of the composition.

The pharmaceutical compositions according to the present invention can be prepared using conventional techniques and equipment. For instance formulations comprising at least one API combined with at least one polyalkoxylated alcohol of the present invention can be obtained by solution-based methods such as co-precipitation and spray drying. For spray drying a solution or dispersion comprising the at least one API and the at least one polyalkoxylated alcohol may be provided and sprayed into a heated gaseous drying medium to evaporate the solvent. Alternatively, also freeze-drying can be applied. Details of the spray drying process can e.g. be found in R. H. Perry, D. W. Green, J. O. Maloney eds., Perry's Chemical Engineers' Handbook, 6th edition, McGraw-Hill Book Co. 1984, pages 20-57. Co-precipitation can be carried out for instance by dissolving the at least one API and the at least one polyalkoxylated alcohol in a mutual solvent and subsequent mixing with a non-solvent or again by removing the solvent through evaporation. Another possibility is to provide a first solution of the API component in a first solvent and a second solution of the polyalkoxylated alcohol component in a second solvent. The first solvent and the second solvent can be selected in such a manner that the solubility of both components is sufficiently low in the mixture of the first and the second solvent. Thus the at least one API and the at least one polyalkoxylated alcohol can be co-precipitated by mixing both solutions. In another possibility, the first solvent and the second solvent can be selected in such a manner that the solubility of both components is sufficiently high in the mixture of the first and the second solvent, and mixing of both solutions gives a clear solution of both components. Alternatively, the same solvent can be selected for dissolution of both components. Removal of the solvent(s) provides a solid or semi-solid mixture of the components. Furthermore the at least one API and the one or more polyalkoxylated alcohols may be combined into a formulation by a melt process. For instance the at least one API may be dissolved in the molten polyalkoxylated alcohol or a mixture of multiple polyalkoxylated alcohols using conventional melt extrusion techniques. The optional additives, if any, may be incorporated at any suitable stage of the preparation of the inventive pharmaceutical compositions such as by including them into the precursor solutions or dispersions or the feedstocks for melting, by adding them during the process used for combining the least one API and the one or more polyalkoxylated alcohols or by introducing them into the mixture obtained from this process. In the obtained product of the aforementioned preparation processes the API and polyalkoxylated alcohol components may be present as a solid dispersion or the API may be dissolved in the phase comprising the one or more polyalkoxylated alcohols or be dispersed therein, wherein the dispersed API phase preferably exhibits a size of less than 1 m in all dimensions, without being limited thereto. The pharmaceutical compositions of the present invention as prepared by any one of these preparation processes are typically obtained in solid or semi-solid form e.g. as a solidified extrudate, a powder or mass of gel- or paste-like consistency and may thus be in particular conveniently used to provide solid or semi-solid dosage forms comprising a pharmaceutical compositions according to the present invention. The solid dosage form can e.g. be a powder, a lozenge, a suppository, a tablet or a filled capsule. Suitable semi-solid dosage forms can be exemplified by gels, creams, pastes and ointments.

For oral administration tablets and capsules have particularly good acceptance among most patients and are thus preferably used as delivery system. Tablets comprising the pharmaceutical composition of the present invention may readily be prepared by conventional pressing of the raw powder or melt extrusion of the pharmaceutical composition and re-solidification using dies of the desired tablet size and shape. In case the as prepared composition is semi-solid one or more fillers, which can be of the above-mentioned type, may be added for thickening in order to achieve the desired consistency for providing tablets. Capsules filled with the pharmaceutical composition according to the present invention may be prepared using processing techniques and equipment, which is per se known from the prior art, e.g. from E. T. Cole, Advanced Drug Delivery Reviews 60 (2008), 747-756. Both capsules of the soft type and of the hard type can be used to encapsulate the inventive pharmaceutical compositions. Soft capsules are typically formed and filled in one operation using a rotary die and have a shell consisting of a single piece. Hard capsules are usually manufactured separately and consist of a cap and a body. The empty body may be filled with the targeted amount of the pharmaceutical composition according to the present invention e.g. in powder form or as hot extruded melt.

Subsequently the cap is attached and the capsule sealed e.g. by applying a band of adhesive material at the body/cap interface or by moisturizing the contact area between body and cap, heating and setting. The capsule shell material comprises typically gelatin as main constituent although alternative materials such as hydroxypropyl methylcellulose, iota carrageenan, hydroxypropyl starch, polyvinyl alcohol and starch may also be used. The shell may include additional substances e.g. plasticizers such as water or glycerol, coloring agents and opacifiers.

EXAMPLES

Synthesis of Amino Alcohol Starter

This synthesis of amino alcohol starter BA-DGE/DBA described below is representative of the synthesis of all of the amino alcohol starters. The other starters can be synthesized according to similar procedures. To a 30 mL vial containing a cross-shaped stir bar was added bisphenol-A diglycidyl ether (D.E.R. 331 epoxy resin, 7.40 g of epoxide equivalent weight=185 g/mol epoxide, 40.0 millimole (mmol) epoxide) and dibutylamine (5.16 g, 40.0 mmol, 40.0 mmol N—H). The vial was capped with an inverted 14/20 septum that was secured with copper wire. A syringe needle was inserted through the septum to vent the reaction. The reaction mixture was heated at 75° C. for 30 min, 130° C. for 2 h, and 150° C. for 2 h. The product was a clear, light yellow, viscous liquid. $^1H$ and $^{13}C$ NMR analysis of the product was consistent with the structure of amino alcohol BA-DGE/DBA. The yield was quantitative.

Synthesis of Polyalkoxylated Amino Alcohols.

The reactions are carried out in a parallel port reactor (PPR) setup containing a plate with 48 (6×8) small reactors 24 of which located in three separate modules were utilized. Propylene oxide (PO) and ethylene oxide (EO) are delivered via an ISCO syringe pump equipped with a robotically controlled needle and compressed gas micro-valve.

A glass insert along with a removable poly(ether ether ketone) (PEEK) stir paddle for each cell are dried in a vacuum oven at 125° C. The stock solutions of the starters which are listed below were prepared in o-xylene. Potassium hydride (KH) was added to each solution with stirring overnight to produce >50 mol % of the alkoxyde as shown below:

|  | Amount (g) | o-Xylene (g) | Total (g) | KH (mg) | KH (mmol) |
| --- | --- | --- | --- | --- | --- |
| BA-DGE/DBA | 2.85 | 3.18 | 6.03 | 100 | 2.5 |
| BA-DGE/2EHA | 2.84 | 3.51 | 6.35 | 80 | 2 |
| h-BA-DGE/DBA | 2.85 | 3.36 | 6.21 | 100 | 2.5 |
| BD-DGE/DBA | 2.9 | 2.79 | 5.69 | 150 | 3.75 |

The stock solutions of the starters are charged manually using a pipette into the glass inserts under nitrogen. The amounts of the stock solutions range from 1.0 to 2.0 ml for all cells.

The glass inserts along with the stir paddles are loaded to the corresponding PPR wells and the reactors were sealed. The cells are charged with calculated amounts of propylene oxide. The temperature is increased to 150° C. and reaction mixtures are stirred for 4 hours after reaching the process temperature. The pressure profile indicated when the reactions were completed. The cells are vented and purged with nitrogen to remove residual propylene oxide. The system is left overnight.

Next day, reactor modules are heated to 70° C., ethylene oxide is introduced, the temperature was increased to 150° C. and the reactors were stirred for 4 hrs. The pressure curves were consistent with reaction completion. After cooling and venting as described above, the mixtures are quenched with 10 wt % acetic acid in o-xylene. Then small samples were taken from each reactor for NMR analyses from which is determined the average number of PO and EO units.

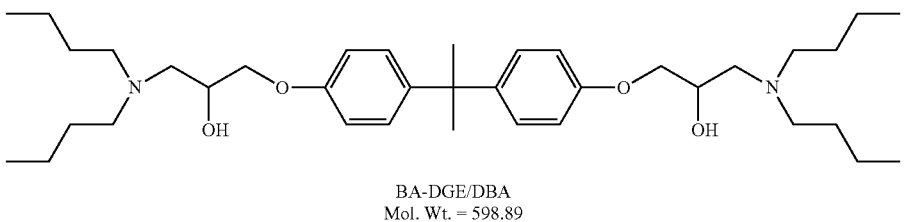

BA-DGE/DBA
Mol. Wt. = 598.89

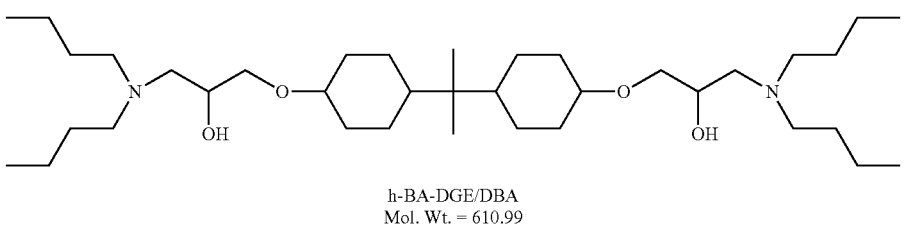

h-BA-DGE/DBA
Mol. Wt. = 610.99

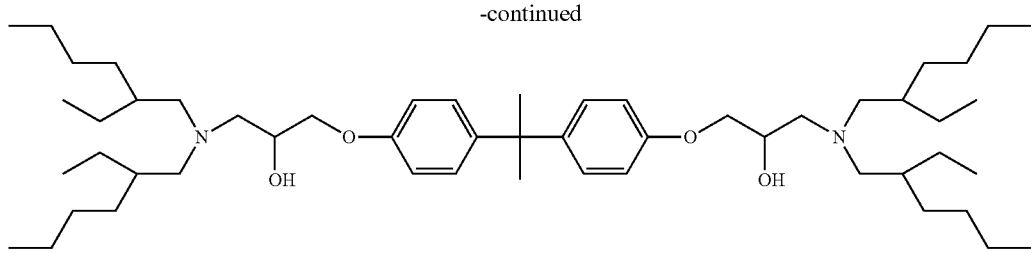

BA-DGE/2EHA
Mol. Wt. = 823.33

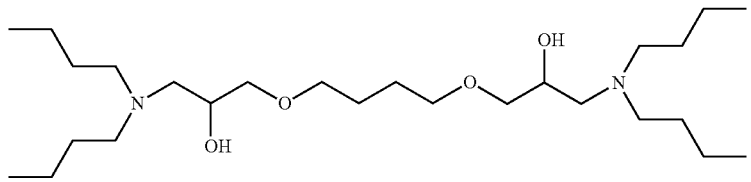

BD-DGE/DBA
Mol. Wt. = 460.73

Examples 1-15 and Comparative Examples 1 and 2

A concentrate solution of 1 wt % difenoconazole and with no additive (Comparative 1 and 2) or either 10 wt % or 1 wt % polyalkoxylated amino alcohols is prepared. This is diluted with water such that the amount of the difenoconzole is 500 ppm and the amount of the polyalkyoxylated amino alcohol is either 500 ppm or 5000 ppm. The mixtures are measured for light transmission for 25 hours using a Turbiscan™ tower. The height averaged transmission over the bottom ⅓ of the solution, normalized using the height averaged from the bottom ⅓ of the control transmission (which is made up of the alkyoxylated amino alcohol and solvent (if any) and water in concentrations in the same range as when tested with the active present). Results are shown in Table 1.

Difenoconazole Structure

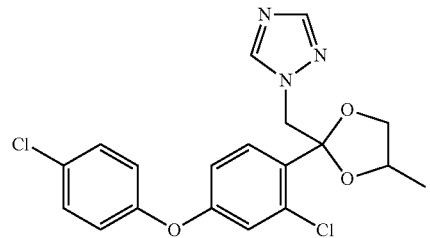 [SMILES: CC1COC(Cn2cncn2)(c2ccc(Oc3ccc(Cl)cc3)cc2Cl)O1]

TABLE 1

| | | | Difenoconazole Results | | | | | | |
|---|---|---|---|---|---|---|---|---|---|
| | | Additive | | | | | | | |
| Example | Starter | Type of AO | Average number of PO groups/average number of EO groups on a per molecule basis | Amount of additive (ppm) | Time (hours) | | | | |
| | | | | | 0 | 1 | 2 | 4 | 20 |
| 1 | BA-DGE/DBA | block | 82/151 | 5000 | 99 | 99 | 99 | 99 | 99 |
| 2 | BA-DGE/DBA | block | 48/63 | 5000 | 96 | 95 | 95 | 95 | 94 |
| 3 | BA-DGE/DBA | block | 48/63 | 5000 | 100 | 100 | 100 | 99 | 98 |
| 4 | BA-DGE/2EHA | block | 105/162 | 5000 | 98 | 98 | 98 | 98 | 98 |
| 5 | BA-DGE/2EHA | block | 41/66 | 5000 | 98 | 98 | 98 | 98 | 98 |
| 6 | h-BA-DGE/DBA | block | 55/115 | 5000 | 100 | 101 | 101 | 101 | 101 |
| 7 | h-BA-DGE/DBA | block | 33/50 | 5000 | 100 | 100 | 100 | 100 | 100 |
| 8 | BD-DGE/DBA | block | 41/69 | 5000 | 97 | 98 | 98 | 98 | 98 |

TABLE 1-continued

| | | | Difenoconazole Results | | | | | | |
|---|---|---|---|---|---|---|---|---|---|
| | | | Additive | | | | | | |
| Example | Starter | Type of AO | Average number of PO groups/average number of EO groups on a per molecule basis | Amount of additive (ppm) | \multicolumn{5}{c}{Time (hours)} |
| | | | | | 0 | 1 | 2 | 4 | 20 |
| 9 | BD-DGE/DBA | block | 23/36 | 5000 | 97 | 97 | 97 | 97 | 97 |
| 10 | BA-DGE/2EHA | block | 105/162 | 500 | 49 | 19 | 15 | 12 | 20 |
| 11 | BA-DGE/2EHA | block | 41/66 | 500 | 90 | 90 | 90 | 90 | 90 |
| 12 | h-BA-DGE/DBA | block | 55/115 | 500 | 79 | 61 | 54 | 47 | 35 |
| 13 | h-BA-DGE/DBA | block | 33/50 | 500 | 79 | 79 | 78 | 77 | 75 |
| 14 | BD-DGE/DBA | block | 41/69 | 500 | 70 | 65 | 64 | 62 | 56 |
| 15 | BD-DGE/DBA | block | 23/36 | 500 | 39 | 36 | 35 | 34 | 31 |
| CE1 | — | — | — | — | 1 | 0 | 0 | 0 | 1 |
| CE2 | — | — | — | — | 1 | 0 | 0 | 0 | 1 |

Examples 16-37 and Comparative 3

The process of for Examples 1-15 and Comparative 1 and 2 was repeated using this time pyraclostrobin instead of the Difenoconazole. The results are shown in Table 2.

Pyraclostrobin Structure

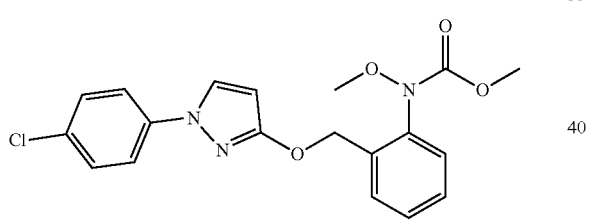

TABLE 2

| | | | Pyraclostrobin Results | | | | | | |
|---|---|---|---|---|---|---|---|---|---|
| | | | Additive | | | | | | |
| Example | Starter | Type | PO/EO | Amount of additive (ppm) | \multicolumn{5}{c}{Time (hours)} |
| | | | | | 0 | 1 | 2 | 4 | 20 |
| 24 | BA-DGE/2EHA | block | 105/162 | 5000 | 87 | 92 | 92 | 92 | 93 |
| 25 | BA-DGE/DBA | block | 82/151 | 5000 | 96 | 96 | 96 | 96 | 96 |
| 26 | BA-DGE/DBA | block | 48/63 | 5000 | 97 | 97 | 97 | 96 | 95 |
| 27 | BD-DGE/DBA | block | 41/69 | 5000 | 90 | 93 | 94 | 94 | 93 |
| 28 | h-BA-DGE/DBA | block | 55/115 | 5000 | 83 | 83 | 86 | 89 | 92 |
| 29 | BA-DGE/2EHA | block | 41/66 | 5000 | 94 | 95 | 95 | 95 | 94 |

TABLE 2-continued

Pyraclostrobin Results

| | | Additive | | Amount of additive | Time (hours) | | | | |
|---|---|---|---|---|---|---|---|---|---|
| Example | Starter | Type | PO/EO | (ppm) | 0 | 1 | 2 | 4 | 20 |
| 30 | h-BA-DGE/DBA | block | 33/50 | 5000 | 96 | 97 | 97 | 97 | 97 |
| 31 | BD-DGE/DBA | block | 23/36 | 5000 | 85 | 89 | 89 | 88 | 85 |
| 32 | BA-DGE/2EHA | block | 105/162 | 500 | 38 | 6 | 2 | 1 | 0 |
| 33 | BA-DGE/2EHA | block | 41/66 | 500 | 45 | 11 | 5 | 2 | 0 |
| 34 | h-BA-DGE/DBA | block | 55/115 | 500 | 69 | 46 | 35 | 24 | 7 |
| 35 | h-BA-DGE/DBA | block | 33/50 | 500 | 84 | 82 | 81 | 79 | 71 |
| 36 | BD-DGE/DBA | block | 41/69 | 500 | 47 | 37 | 33 | 28 | 15 |
| 37 | BD-DGE/DBA | block | 23/36 | 500 | 53 | 25 | 18 | 12 | 3 |
| CE3 | — | — | — | — | 2 | 0 | 0 | 0 | 0 |

The compositions and methods can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

For ranges, stated upper and lower limits can be combined to form ranges (e.g. "at least 1 or at least 2 weight percent" and "up to 10 or 5 weight percent" can be combined as the ranges "1 to 10 weight percent", or "1 to 5 weight percent" or "2 to 10 weight percent" or "2 to 5 weight percent"). The terms "first," "second," and the like, do not denote any order, quantity, or importance, but rather are used to distinguish one element from another. The terms "a" and "an" and "the" do not denote a limitation of quantity and are to be construed to cover both the singular and the plural, unless otherwise indicated herein or clearly contradicted by context. "Or" means "and/or" unless clearly stated otherwise.

Unless specified to the contrary herein, all test standards are the most recent standard in effect as of the filing date of this application, or, if priority is claimed, the filing date of the earliest priority application in which the test standard appears.

The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl, or a cycloalkyl, such as cyclohexyl, or alkyls including cyclic groups and straight or branched chains. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Aryl" means an aromatic hydrocarbon group containing the specified number of carbon atoms, such as phenyl, tropone, indanyl, or naphthyl. The prefix "hetero" means that the compound or group includes at least one ring member that is a heteroatom (e.g., 1, 2, or 3 heteroatom(s)), wherein the heteroatom(s) is each independently N, O, S, Si, or P. The number of carbon atoms indicated in a group is exclusive of any substituents. For example —CH$_2$CH$_2$CN is a C$_2$ alkyl group substituted with a nitrile.

What is claimed is:

1. A composition comprising biologically active compound that is insoluble or poorly soluble in water and a polyalkoxylated amino alcohol of the formula

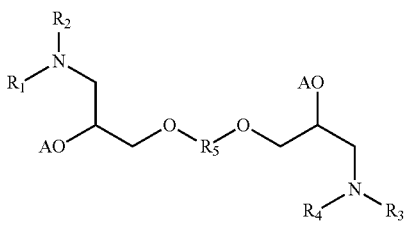

where R$_1$, R$_2$, R$_3$, and R$_4$ are independently selected from alkyl, alkenyl, aryl, aralkyl, or heterocyclic groups having 1-25 carbons, R$_5$ is a divalent alkyl, alkenyl, aryl, aralkyl, or heterocyclic group having 4-25 carbons, and where each AO is a polyoxyalkylene chain having oxypropylene (PO) and oxyethylene (EO) groups, where m is the average number of PO groups per AO group and n is the average number of the average number of EO groups per AO group, and m is at least 1, n is at least 2, and m+n is at least 20 no more than 400, wherein the composition is solid or comprises water.

2. The composition of claim 1 wherein R$_1$, R$_2$, R$_3$, and R$_4$ are independently selected alkyl groups having 3-12 carbon atoms.

3. The composition of claim 1 wherein R$_1$, R$_2$, R$_3$, and R$_4$ are butyl or 2-ethylhexyl.

4. The composition of claim 1 wherein R$_5$ is 2,2-isopropylidenediphenylene, 2,2-isopropylidenedicyclohexylidene, or 1,4-butylene.

5. The composition of claim 1 wherein m is at least 10 and n is at least 15.

6. The composition of claim 1 wherein m/n is less than 1.

7. The composition of claim 1 wherein m is at least 10 and n is at least 15 and m+n is less than 300.

8. The composition of claim 1 wherein AO is a block copolymer of PO and EO.

9. The composition of claim 1 wherein at least one AO has an EO rich block and a PO rich block.

10. The composition of claim 1 further comprising a solvent that is at least partially miscible with water.

11. The composition of claim 1 which is an aqueous solution.

12. The composition of claim 1 wherein the weight ratio of the biologically active compound to the polyalkoxylated amino alcohol is in the range of 2:1 to 1:100.

13. The composition of claim 1 wherein the biologically active compound is an agricultural active ingredient.

14. The composition of claim 1 wherein the biologically active compound is an active pharmaceutical ingredient.

15. A method comprising diluting the composition of claim 13 with water and applying it to an area to prevent pests by spraying.

16. The composition of claim 1 wherein the biologically active compound is difenoconazole.

17. The composition of claim 1 wherein $R_5$ is 2,2-isopropylidenedicyclohexylidene.

18. The composition of claim 1 wherein the biologically active compound is difenoconazole, $R_5$ is 2,2-isopropylidenedicyclohexylidene, m is 33 and n is 50.

* * * * *